United States Patent [19]

Deya et al.

[11] Patent Number: 4,873,229

[45] Date of Patent: Oct. 10, 1989

[54] GALACTO-OLIGOSACCHARIDE CONTAINING FEED

[75] Inventors: Eiki Deya, Sayama; Shuichi Yanahira, Tsurugashimamachi; Kenkichi Abiko; Eiichi Kikuchi, both of Kodaira, all of Japan

[73] Assignee: Snow Brand Milk Products Co., Ltd., Sapporo, Japan

[21] Appl. No.: 939,141

[22] Filed: Dec. 8, 1986

[30] Foreign Application Priority Data

Dec. 12, 1985 [JP] Japan .................................. 60-277957

[51] Int. Cl.$^4$ .................... A61K 31/70; A61K 31/715
[52] U.S. Cl. ......................................... 514/54; 514/53; 514/867; 426/42; 426/43; 426/801; 426/805; 424/442; 536/123

[58] Field of Search ................... 426/42, 43, 801, 805; 424/442; 536/123; 514/53, 54, 867

[56] References Cited

U.S. PATENT DOCUMENTS 4,066,750 1/1978 Smith et al. ........................... 514/42
4,362,710 12/1982 Watanabe ............................ 424/442

FOREIGN PATENT DOCUMENTS 60-34134 2/1985 Japan .

*Primary Examiner*—Ronald W. Griffin
*Attorney, Agent, or Firm*—Fisher, Christen & Sabol

[57] ABSTRACT

A stock feed containing a specific amount of galacto-oligosaccharides, the stock feed being effective in the prevention of scours/loose passage of livestocks and thus in the increase of their weight.

6 Claims, No Drawings

GALACTO-OLIGOSACCHARIDE CONTAINING FEED

BACKGROUND OF THE INVENTION

This invention relates to a stock feed effective in the prevention of scours/loose passage of livestock and the increase of their weight.

Recently, a stock feed has been proposed which contains a saccharide consisting mainly of fructo-oligosaccharides known as a growth stimulator of *Lactobacillus bifidus* in the human intestines (Japanese Patent Laid-Open No. 34134/1985).

However, no report has been published to use galacto-oligosaccharides, a class of the oligosacharides contained in the human milk or cow's milk, as an ingredient of stock feed.

In the course of investigation on the activity of galacto-oligosaccharides with the aim toward developing their new applications, the present inventors observed such a possibility that the oral ingestion of galacto-oligosaccharides by livestock caused useful bacteria belonging to the genus Bacillus or the genus Bacteroides, the principal intestinal bacteria of livestock, to increase and the growth of harmful bacteria such as *Clostridium Perfringeus* (*C. Welchii*) and *Clostridium* was thereby prevented. On the basis of such assumptions, a stock feed incorporated with a specific amount of galacto-oligosaccharides was fed to such livestock as calves. As a result, it was found that the scours/loose passage observed frequently in the course of breeding calves was prevented effectively and their weight increased markedly, leading to the completion of the present invention.

SUMMARY OF THE INVENTION

A main object of the present invention is to provide a stock feed incorporated with galacto-oligosaccharides which is markedly effective in the prevention of scours/loose passage of livestock and the increase of their weight.

A feature of the present invention is in a stock feed containing from 0.1 to 2% by weight of galacto-oligosaccharides.

The term "galacto-oligosaccharides" used in the present invention means galactosyl-lactose formed by joining one mole of galactose to one mole of lactose and digalactosyllactose formed by joining two moles of galactose to one mole of lactose.

DETAILED DESCRIPTION OF THE INVENTION

The galacto-oligosaccharides used as an active ingredient in the present invention can be prepared in the following manner:

β-Galactosidase is allowed to act on lactose or a lactose-containing matter (for instance, whole milk, skim milk, whey, etc.) so as to cause a transgalactosilation, thereby forming a mixture of galacto-oligosaccharides.

The action of β-galactosidase on the aforesaid lactose or lactose-containing matter may properly be effected by allowing the enzyme to act on a substrate formed by adjusting the lactose concentration of the starting material at 5–50%, under the conditions of a pH of 2–8, an enzyme concentration of 0.1–200 units/ml and a temperature of 10–60° C. Since the reaction time for effecting the above enzymatic action exerts a large influence on tee yield of the oligosaccharides, it is necessary to confirm the optimum reaction time by experiments. Specifically, the reaction time is set while determining the amount of galacto-oligosaccharides in the reaction product formed through the above enzymatic action by high-speed liquid chromatography.

The enzymatic reaction can be terminated by heating the reaction liquid above 90° C. for 2–30 seconds. Spray-drying or drum-drying of the enzyme-treated reaction liquid may produce a powder containing 20–50% by weight of the galacto-oligosaccharides.

In the present invention, the galacto-oligosaccharide powder thus obtained is mixed with a stock feed in an amount of 0.1–2% by weight based on the stock feed and the resulting mixture is fed to livestock. Any stock feeds known per se in the art may be used for this purpose.

If the amount of the galacto-oligosaccharides is less than 0.1% by weight relative to the stock feed, no significant effects will be recognized in the prevention of scours/loose passage of livestocks. On the other hand, any amounts in excess of 2% by weight will not improve substantially the effects on the prevention of the scours/loose passage and on the increase of livestocks'-weight and thus are not economical.

In other words, incorporation of galacto-oligosaccharides in a stock feed in an amount of 0.1–2% by weight relative to the stock feed makes it possible to increase the weight of livestock as well as to prevent scours/loose passage of livestock in an efficient manner.

The present invention and its effects are described below more specifically with reference to the following example.

EXAMPLE

Preparation of galacto-oligosaccharides

Citric acid was added to a solution formed by dissolving 100 kg of lactose (commercial product) in 150 kg of warm water to adjust the pH of the solution at 4.5. To the resulting solution was added 0.5 million units of β-galactosidase, thereby causing the reaction at 40° C. for 10 hours. The resulting liquid reaction mixture was heated at 105° C. for two seconds so as to deactivate the enzyme and thereafter subjected to spray-drying to prepare a powder containing 50% by weight of galacto-oligosaccharides.

Incorporation of galacto-oligosaccharides in a stock feed

The oligosaccharide powder prepared as described above was added to a stock feed having the below-described composition in such a manner that five samples of the stock feed contain individually 0.05%, 0.1%, 2%, 3% and 5% by weight of galacto-oligosaccharides, thus preparing five feed samples for calves in the weaning period.

| | |
|---|---|
| Whole milk powder | 50 parts by weight |
| Skim milk powder | 20 parts by weight |
| Vitamins and minerals | 3 parts by weight |

Feeding test of calves

The five feed samples prepared as described above, each of which is different in the content of galacto-oligosaccharides, were fed to calves according to the undermentioned method so as to measure the occurrence rate of scours/loose passage and the increasing rate of weight. Measurements were also made in the case of feeding calves similarly with a feed sample containing 0.1% by weight of fructo-oligosaccharides in place of galacto-oligosaccharides as a comparison and a feed sample containing no oligosaccharides as a control.

Test method

The above feed samples were fed individually to calves in the test areas, each of which holds 20 male Holstein calves of one week old, so as to feed the calves for 3 weeks. During this period, the occurrence rate of scours/loose passage and the increasing rate of weight of the calves in each of the test areas were measured.

The results are as shown in the following table.

TABLE

| | | | Test Area | | | | |
|---|---|---|---|---|---|---|---|
| | Control area | Fructo-oligo-saccharide Area (0.1%) | Galacto-oligosaccharide Area | | | | |
| Item | | | 0.05% | 0.1% | 2% | 3% | 5% |
| Weight before feeding (kg) | 40 | 42 | 43 | 40 | 42 | 43 | 45 |
| Average Weight Increase (kg/head) | 10 | 11 | 11 | 15 | 16 | 18 | 17 |
| Occurrence Rate of Scours/ Loose Passage (%) | 80 | 75 | 75 | 50 | 15 | 16 | 15 |
| Demanding Rate of Feed (%) | 0.65 | 0.60 | 0.59 | 0.49 | 0.47 | 0.47 | 0.47 |

(Note)
The percentages (%) in Galacto-oligosaccharide Area and the percentage (%) in the Fructo-digosaccharide Area indicate the content of galacto-oligosaccharides in the feed samples and the content of fructo-oligosaccharides in the comparison feed sample, respectively.

As can be seen in the Table, a lower occurrence rate of scours/loose passage and a higher increasing rate of weight were observed in the test area in which the feed sample containing 0.1% by weight of galacto-oligosaccharides was used than in the test areas in which the control feed sample and the feed sample containing the same amount of fructo-oligosaccharides were individually used.

Further, no particular improvements are observed in the effect of increasing the content of galacto-oligosaccharides when the content exceeds 2% by weight.

What is claimed is:

1. A galacto-oligosaccharide containing stock feed which comprises a livestock feed incorporated from about 0.1 to 2% by weight of galacto-oligosaccharides being selected from the group consisting of galactosyl-lactose and digalactosyl-lactose.

2. The stock feed as claimed in claim 1 wherein the galacto-oligosaccharides comprise galactosyl-lactose.

3. The stock feed as claimed in claim 1 wherein the galacto-oligosaccharides comprise digalactosyl-lactose.

4. A method of preventing scours/loose passage in livestock comprising administering thereto a livestock feed comprising 0.1 to 2% by weight of galacto-oligosaccharides relative to the livestock feed.

5. A method as in claim 4 wherein said galacto-oligosaccharide is galactocyl-lactose.

6. A method as in claim 4 wherein said galacto-oligosaccharide is digalactosyl lactose.

* * * * *